United States Patent
Li et al.

(10) Patent No.: US 9,675,800 B2
(45) Date of Patent: Jun. 13, 2017

(54) SNORE STOPPING DEVICE

(71) Applicant: BOE TECHNOLOGY GROUP CO., LTD., Beijing (CN)

(72) Inventors: Yanjun Li, Beijing (CN); Yingzi Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/139,630

(22) Filed: Apr. 27, 2016

(65) Prior Publication Data

US 2017/0056651 A1    Mar. 2, 2017

(30) Foreign Application Priority Data

Aug. 28, 2015   (CN) .......................... 2015 1 0542688

(51) Int. Cl.
  *A61N 1/00*  (2006.01)
  *A61N 1/36*  (2006.01)
  *A61B 5/00*  (2006.01)
  *A61N 1/04*  (2006.01)
  *A61F 5/56*  (2006.01)
  *A61B 7/00*  (2006.01)

(52) U.S. Cl.
  CPC .......... *A61N 1/3601* (2013.01); *A61B 5/4806* (2013.01); *A61B 5/4836* (2013.01); *A61F 5/56* (2013.01); *A61N 1/0456* (2013.01); *A61N 1/0476* (2013.01); *A61N 1/36014* (2013.01); *A61B 7/003* (2013.01)

(58) Field of Classification Search
  CPC .............. A61N 1/33601; A61N 1/0456; A61N 1/0476; A61N 1/36014; A61B 5/4806; A61B 5/4836; A61B 7/003; A61F 5/56
  See application file for complete search history.

(56) References Cited

U.S. PATENT DOCUMENTS

2014/0228905 A1 * 8/2014 Bolea .................. A61N 1/0556
607/42

FOREIGN PATENT DOCUMENTS

| CN | 201642503 U | 11/2010 |
|---|---|---|
| CN | 103705333 A | 4/2014 |
| CN | 104146713 A | 11/2014 |

(Continued)

OTHER PUBLICATIONS

First Office Action dated Oct. 10, 2016 corresponding to Chinese application No. 201510542688.0.

*Primary Examiner* — George Manuel
(74) *Attorney, Agent, or Firm* — Nath, Goldberg & Meyer; Joshua B. Goldberg

(57) ABSTRACT

The embodiments of the invention provide a snore stopping device. The snore stopping device comprises a sleep information acquisition module used for acquiring actual sleep information of a user; a processing module used for comparing the actual sleep information acquired by the sleep information acquisition module with a normal sleep information range, and capable of generating a trigger signal when the actual sleep information goes beyond the normal sleep information range; and an electric stimulation module used for contacting the skin of the user and generating an electric stimulation signal according to the trigger signal. The snore stopping device can effectively cause the snoring user to change his/her sleeping posture, so as to achieve the snore stopping effect.

12 Claims, 1 Drawing Sheet

(56) References Cited

FOREIGN PATENT DOCUMENTS

| | | |
|---|---|---|
| CN | 204233577 U | 4/2015 |
| CN | 204562098 U | 8/2015 |

* cited by examiner

SNORE STOPPING DEVICE

CROSS-REFERENCE TO RELATED APPLICATION

This application claims priority to Chinese Patent Application No. 201510542688.0, filed on Aug. 28, 2015, the contents of which are incorporated by reference in the entirety.

FIELD OF THE INVENTION

The present invention relates to the field of wearable health devices, and specifically relates to a snore stopping device.

BACKGROUND OF THE INVENTION

In recent years, the incidence rate of sleep breathing disorders is on the rise, and sleep apnea syndrome (i.e. snore) is one of the most common sleep breathing disorders. Studies have found that the sleep apnea syndrome has the risks of causing angina and myocardial infarction, increasing cerebral thrombosis, accelerating atherosclerosis and the like. As for children, the sleep apnea syndrome may result in abnormal development (particularly abnormity of facial development), low cognitive and behavioral capabilities and the like. In view of the above, it is necessary to design a snore stopping device to prevent snoring. As we know now, snore can be effectively suppressed by adjusting the sleeping posture.

A snore stopping device is proposed in the patent application publication No. CN204233577U, including a sleep aiding module, an electrocardiograph detection module, a respiration detection module, a temperature detection module, a snore stopping module and a controller, which are arranged on a wearable vest, and the snore stopping module is a vibrating motor. The snore stopping device can be used for monitoring the body temperature, heart rate and respiration signals and controlling the motor to vibrate according to the monitoring results, so that a user changes his sleeping posture to achieve the snore stopping purpose. However, in the presence of an obstacle such as clothes and the like, the effect of reminding the user to change his sleeping posture by means of motor vibration is not obvious.

SUMMARY OF THE INVENTION

An object of the present invention is to provide a snore stopping device, to effectively achieve the snore stopping effect.

To achieve the above object, the embodiments of the present invention provide a snore stopping device, including:

a sleep information acquisition module, used for acquiring an actual sleep information of a user;

a processing module, used for comparing the actual sleep information acquired by the sleep information acquisition module with a normal sleep information range, and generating a trigger signal when the actual sleep information goes beyond the normal sleep information range; and an electric stimulation module, used for contacting the skin of the user and generating an electric stimulation signal according to the trigger signal.

Preferably, the actual sleep information is a volume of snore produced by the user during sleep, and the sleep information acquisition module includes a volume detecting device for detecting the volume of the snore.

Preferably, the electric stimulation module includes:

a stimulation control unit, used for generating a control signal according to the trigger signal;

an electric signal generating unit, used for generating an electric signal of preset voltage according to the control signal, and lasting the electric signal of the preset voltage for preset stimulation time; and a stimulation electrode, used for contacting skin of the user and capable of generating the electric stimulation signal in a manner of discharging to the skin of the user after receiving the electric signal of the preset voltage.

Preferably, the stimulation electrode includes a plurality of electrode plates and a pad for wrapping the electrode plates, the pad is provided therein with openings, the electrode plates are electrically connected with the electric signal generating unit, and at least part of each of the plurality of electrode plates is exposed by the opening to contact the skin of the user.

Preferably, a conductive adhesive is arranged on the surface of the part of the electrode plate exposed by the openings.

Preferably, the electric signal generating unit includes a signal generator, which is electrically connected with the stimulation control unit and the stimulation electrode, respectively, and used for generating the electric signal of the preset voltage.

Preferably, the sleep information acquisition module is capable of periodically acquiring the actual sleep information of the user;

the trigger signal includes a first trigger signal and a second trigger signal, wherein when the sleep information acquisition module acquires the actual sleep information going beyond the normal sleep information range for the first time, the processing module generates the first trigger signal; after the processing module generates the first trigger signal, the processing module counts the number of occurrences of the actual sleep information going beyond the normal sleep information range within a preset acquisition time period from the time when the first trigger signal is generated, and generates the second trigger signal when the number of occurrences is greater than or equal to a preset value;

the control signal includes a first control signal corresponding to the first trigger signal and a second control signal corresponding to the second trigger signal; and the preset voltage includes a first preset voltage corresponding to the first control signal and a second preset voltage corresponding to the second control signal, and the second preset voltage is greater than the first preset voltage.

Preferably, the electric signal generating unit includes a signal generator, a first switch, a second switch and an amplifier;

a control terminal of the first switch is connected with an output terminal of the stimulation control unit, an input terminal of the first switch is connected with an output terminal of the signal generator, an output terminal of the first switch is connected with the stimulation electrode, a control terminal of the second switch is connected with the output terminal of the stimulation control unit, an input terminal of the second switch is connected with the output terminal of the signal generator, an output terminal of the second switch is connected with an input terminal of the amplifier, an output terminal of the amplifier is connected with the stimulation electrode, and an input terminal of the signal generator is connected with the output terminal of the stimulation control unit; the first control signal can control the first switch to be switched on and the second switch to be switched off, and the second control signal can control the first switch to be switched off and the second switch to be switched on; and the signal generator is used for generating an electric signal of the first preset voltage, and the amplifier can amplify the electric signal of the first preset voltage into an electric signal of the second preset voltage.

Preferably, the trigger signal further includes a third trigger signal, and the processing module counts the number of occurrences of the actual sleep information going beyond the normal sleep information range within a preset acquisition time period from the time when the second trigger signal is generated, and generates the third trigger signal when the number of occurrences is greater than or equal to the preset value; and the snore stopping device further includes an audio play module, which is used for sending out an audio signal according to the third trigger signal.

Preferably, the snore stopping device further includes a setting module, which is used for setting the preset stimulation time, the preset acquisition time period, the preset value, the first preset voltage and the second preset voltage.

Preferably, the snore stopping device further includes a storage module, which is used for storing the actual sleep information acquired by the sleep information acquisition module.

Preferably, the snore stopping device further includes a mounting shell, and the sleep information acquisition module, the processing module, the electric signal generating unit and the stimulation control unit are all mounted in the mounting shell.

Preferably, the mounting shell includes a wristband, a finger ring or a head band.

In the embodiments of the present invention, when the actual sleep information acquired by the sleep information acquisition module goes beyond the normal sleep information range, it indicates that the user is snoring, then the processing module may generate a trigger signal, and the electric stimulation module generates an electric stimulation signal according to the trigger signal. As the electric stimulation signal can directly stimulate the skin of the user, so that the user feels pain or itch, in this way, the user can be effectively stimulated to change his/her sleeping posture, and the snore stopping purpose is thus achieved.

BRIEF DESCRIPTION OF THE DRAWINGS

The accompanying drawings are used for providing a further understanding of the present invention, constituting a part of the specification, and interpreting the present invention together with specific embodiments below, rather than limiting the present invention. In the drawings.

DESCRIPTION OF THE PREFERRED EMBODIMENT

The specific embodiments of the present invention will be described in detail below in combination with the accompanying drawings. It should be understood that the specific embodiments described herein are merely used for describing and explaining the present invention, rather than limiting the present invention.

Figure 1:
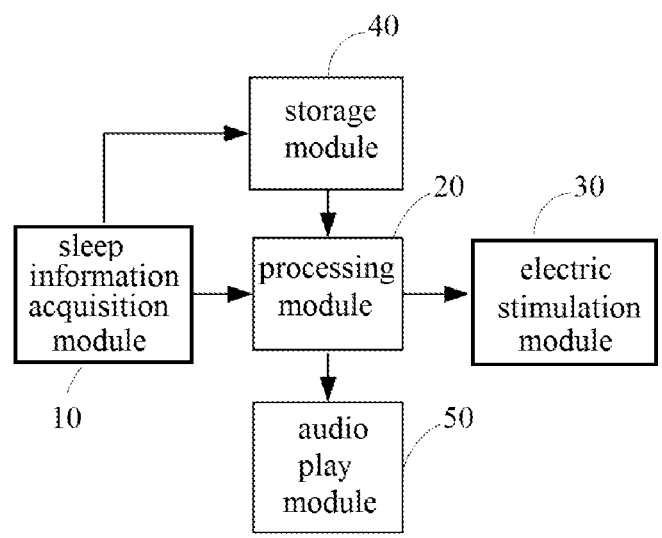
FIG. 1 is a schematic structural diagram of a snore stopping device in an embodiment of the present invention.

As an aspect of the present invention, there is provided a snore stopping device, as shown in FIG. 1, including:

a sleep information acquisition module 10, used for acquiring an actual sleep information of a user;

a processing module 20, used for comparing the actual sleep information acquired by the sleep information acquisition module with a normal sleep information range, and generating a trigger signal when the actual sleep information goes beyond the normal sleep information range; and an electric stimulation module 30, used for contacting the skin of the user and generating an electric stimulation signal according to the trigger signal to apply electric stimulation to the skin of the user.

In the embodiments of the present invention, normal sleep information refers to physiological information of an ordinary people without snoring, and the physiological information includes the respiratory frequency, heart rate, breath sound and the like. It could be understood that the respiratory frequency, the heart rate and the like of a snoring person are somewhat different from those of an ordinary people without snoring. When the actual sleep information acquired by the sleep information acquisition module 10 goes beyond the normal sleep information range, it indicates that a user is snoring, then the processing module 20 may generate a trigger signal, and the electric stimulation module 30 generates an electric stimulation signal according to the trigger signal, so that the user changes his/her sleeping posture after experiencing electric stimulation, to thereby achieve the snore stopping purpose. As the electric stimulation signal can directly stimulate the skin, and cause the user to feel pain or itch, it can effectively cause the user to change his/her sleeping posture, and thus the snore stopping purpose is achieved.

The sleep information may include the respiratory frequency, heart rate and the like, and the sleep information acquisition module 10 may be implemented in different forms to acquire the actual sleep information of different forms.

Preferably, the actual sleep information may be the volume of snore produced by the user during sleep, to facilitate acquisition of the actual sleep information. In this case, the normal sleep information may include a normal volume range of sound produced by a person during sleep without snoring. Correspondingly, the sleep information acquisition module 10 includes a volume detecting device, which is used for detecting the volume of snore produced by the user during sleep. Generally, when a person is in sleep, the surrounding environment is quiet, so the volume detecting device can detect the volume of sound at the position of the user as the volume of snore produced by the user during sleep. Specifically, the normal volume range is 0-40 dB, that is to say, when the volume detecting device detects that the volume of snore produced by the user is greater than 40 dB, the processing module 20 generates the trigger signal.

Specifically, the electric stimulation module 30 includes:

a stimulation control unit 31, used for generating a control signal according to the trigger signal;

an electric signal generating unit 32, used for generating an electric signal of preset voltage according to the control signal and lasting the electric signal of the preset voltage for preset stimulation time; and a stimulation electrode 33, used for contacting the skin of the user and capable of generating the electric stimulation signal in a manner of discharging to the skin of the user after receiving the electric signal of the preset voltage.

When the actual sleep information of the user goes beyond the normal sleep information range, that is, when it is determined that the user is snoring, the trigger signal is generated, and, at this time, the stimulation control unit 31 generates the control signal according to the trigger signal, and the electric signal generating unit 32 generates the electric signal of preset voltage, then the electric signal generating unit 32, the stimulation electrode 33 and the human body form a current path, and electric stimulation is applied to the user by releasing charges to the human body.

It could be understood that the value of the preset voltage should not be too large, so as to prevent harm to the human body. The preset stimulation time may be determined according to actual conditions, such that the user can be simulated to change his/her sleeping posture without influencing his/her continued sleep. For example, the preset stimulation time may range from half a minute to one minute.

Figure 3:
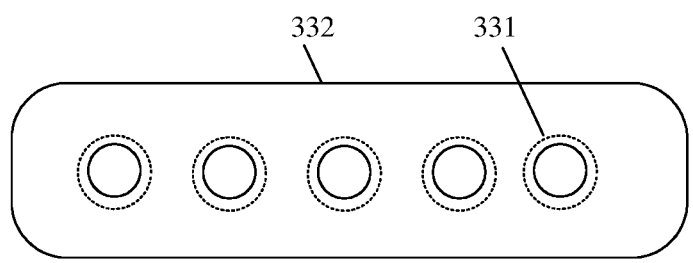
FIG. 3 is a schematic structural diagram of a stimulation electrode in an embodiment of the present invention.

Specifically, as shown in FIG. 3, the stimulation electrode 33 may include a plurality of electrode plates 331 and a pad 332 for wrapping the electrode plates 331, the pad 332 is provided therein with openings, the electrode plates 331 are electrically connected with the electric signal generating unit, and a part of each of the plurality of electrode plates 331 is exposed by the opening so as to contact the skin of the user. As shown in FIG. 3, circles shown by dotted lines represent the electrode plates, and circles shown by solid lines represent the openings.

Further, a conductive adhesive may be arranged on the surface of the part of the electrode plate exposed by the opening, so that the electrode plate can be stably adhered to the skin of the user, so as to ensure that the user feels electric stimulation.

Specifically, the electric signal generating unit 32 includes a signal generator 321 (e.g. a pulse signal generator), which is electrically connected with the stimulation control unit 31 and the stimulation electrode 33, respectively, and used for generating the electric signal of the preset voltage.

Further, the sleep information acquisition module 10 can periodically acquire the actual sleep information of the user.

The trigger signal includes a first trigger signal and a second trigger signal, wherein when the sleep information acquisition module 10 acquires the actual sleep information going beyond the normal sleep information range for the first time, the processing module 20 generates the first trigger signal; after the processing module 20 generates the first trigger signal, the processing module counts the number of occurrences of the actual sleep information going beyond the normal sleep information range within a preset acquisition time period from the time when the first trigger signal is generated, and generates the second trigger signal when the number of occurrences is greater than or equal to a preset value.

Correspondingly, the control signal includes a first control signal corresponding to the first trigger signal and a second control signal corresponding to the second trigger signal; the preset voltage includes a first preset voltage corresponding to the first control signal and a second preset voltage corresponding to the second control signal, and the second preset voltage is greater than the first preset voltage.

Thus, after the processing module 20 generates the first trigger signal (that is, it is determined that the user is snoring), the stimulation electrode 33 generates an electric stimulation signal corresponding to the first preset voltage, and within a preset acquisition time period from the time when the electric stimulation signal is generated, if the number of occurrences of the actual sleep information going beyond the normal sleep information range is greater than or equal to the preset value, it is judged that the user does not adjust his/her sleeping posture within the preset acquisition time period or continues snoring after adjusting his/her sleeping posture, which indicates that the electric stimulation effect is not obvious. In this case, the processing module 20 generates the second trigger signal, so that the stimulation control unit 31 generates the second control signal so as to control the electric signal generating unit 32 to generate an electric signal of higher preset voltage (i.e. an electric signal of the second preset voltage), and then the stimulation electrode applies higher electric stimulation (i.e. generates the electric stimulation signal corresponding to the second preset voltage) to the human body, so that the user feels stronger pain or itch and changes his/her sleeping posture to achieve the snore stopping effect.

For example, the user starts the snore stopping device at 23:00 at night, the sleep information acquisition module 10 acquires actual sleep information every 15 minutes, the preset acquisition time period is 2 hours, and the preset value is 5. At 24:00 at night, the processing module 20 determines that the actual sleep information goes beyond the normal sleep information range, then the processing module 20 sends out the first trigger signal, and the electric stimulation module 30 applies electric stimulation corresponding to the first preset voltage to the user. If actual sleep information is acquired by the sleep information acquisition module 10 eight times between 24:00 and 2:00 a.m., and the actual sleep information goes beyond the normal sleep information range five times, the processing module 20 generates the second trigger signal, and then the electric stimulation module 30 generates the electric stimulation signal corresponding to the second preset voltage to apply electric stimulation to the user.

As mentioned above, the electric signal generating unit 32 may include a signal generator, wherein in the case where the control signal includes a first control signal and a second control signal, the signal generator may generate a first preset voltage according to the first control signal or generate a second preset voltage according to the second control signal. Alternatively, the electric signal generating unit 32 may include other structure to generate electric signals of different preset voltages.

Figure 2:
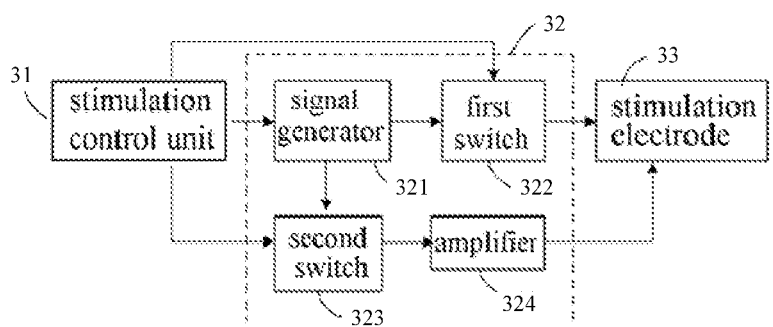
FIG. 2 is a schematic structural diagram of an electric stimulation module in an embodiment of the present invention.

As a specific embodiment of the present invention, as shown in FIG. 2, the electric signal generating unit 32 includes a signal generator 321, a first switch 322, a second switch 323 and an amplifier 324, wherein the control terminal of the first switch 322 is connected with the stimulation control unit 31, the input terminal of the first switch 322 is connected with the output terminal of the signal generator 321, and the output terminal of the first switch 322 is connected with the stimulation electrode 33; the control terminal of the second switch 323 is connected with the stimulation control unit 31, the input terminal of the second switch 323 is connected with the output terminal of the signal generator 321, the output terminal of the second switch 323 is connected with the input terminal of the amplifier 324, the output terminal of the amplifier 324 is connected with the stimulation electrode 33, and the input terminal of the signal generator 321 is connected with the output terminal of the stimulation control unit 31; the first control signal can control the first switch 322 to be switched on and the second switch 323 to be switched off; and the second control signal can control the first switch 322 to be switched off and the second switch 323 to be switched on.

The signal generator 321 is used for generating the electric signal of the first preset voltage, and the amplifier 324 can amplify the electric signal of the first preset voltage to the electric signal of the second preset voltage. The amplifier 324 may be an operational amplifier, which can linearly amplify the voltage signal well and thus amplifies the small first preset voltage to the large second preset voltage.

Thus, in the case that the sleep information acquisition module 10 begins acquiring the actual sleep information, when the actual sleep information of the user goes beyond the normal sleep information range, the processing module 20 can generate a first trigger signal, the stimulation control unit 31 generates a first control signal according to the first trigger signal so that the first switch 322 is switched on and the second switch 323 is switched off, the signal generator 321 is electrically connected to the stimulation electrode 33, and the electric signal of the first preset voltage generated by the signal generator 321 is output to the stimulation electrode 33 through the first switch 322, so that the stimulation electrode 33 generates an electric stimulation signal corresponding to the first preset voltage and used for applying electric stimulation to the human body. When the number of occurrences of the actual sleep information, acquired by the sleep information acquisition module 10, going beyond the normal sleep information range exceeds a preset value within a preset acquisition time period, the processing module 20 generates a second trigger signal, and the stimulation control unit 31 generates a second control signal according to the second trigger signal, so that the second switch 323 is switched on and the first switch 322 is switched off; the signal generator 321, the amplifier 324 and the stimulation electrode 33 are electrically connected with each other; the amplifier 324 amplifies the electric signal of the first preset voltage generated by the signal generator 321 to the electric signal of the second preset voltage, and outputs the electric signal of the second preset voltage to the stimulation electrode 33, so that the stimulation electrode 33 generates the electric stimulation signal corresponding to the second preset voltage and used for applying electric stimulation to the human body.

The first switch may be an N-type thin film transistor, the second switch may be a P-type thin film transistor, and the gate, source and drain of the N-type thin film transistor correspond to the control terminal, input terminal and output terminal of the first switch, respectively. The gate, source and drain of the P-type thin film transistor correspond to the control terminal, input terminal and output terminal of the second switch, respectively. Accordingly, the first control signal is a high-level signal, and the second control signal is a low-level signal. Alternatively, the first switch may be a P-type thin film transistor, the second switch may be an N-type thin film transistor, and accordingly the first control signal is a low-level signal, and the second control signal is a high-level signal. The first and the second switches of the present invention are not limited to the above implementations, as long as the first control signal can switch on the first switch and switch off the second switch, and the second control signal can switch on the second switch and switch off the first switch.

The trigger signal may further include a third trigger signal. After the second trigger signal is generated, the processing module 20 counts the number of occurrences of the actual sleep information going beyond the normal sleep information range within a preset acquisition time period from the time when the second trigger signal is generated, and generates the third trigger signal when the number of occurrences exceeds the preset value.

The snore stopping device further includes an audio play module 50, which is used for sending out an audio signal according to the third trigger signal.

The audio signal may be pre-stored music. When the number of occurrences of the actual sleep information going beyond the normal sleep information range within the preset acquisition time period from the time when the processing module 20 generates the second trigger signal is greater than or equal to the preset value, the third trigger signal is generated, which indicates that the user still does not adjust his/her sleeping posture or still snores after adjusting his/her sleeping posture after receiving the electric stimulation signal corresponding to the second preset voltage; then sound stimulation is provided to the user by playing audio, so as to make the user change his/her sleeping posture.

In the above example, the sleep information acquisition module acquires actual sleep information every 15 minutes, the preset acquisition time period is 2 hours, and the preset value is 5; the processing module 20 generates the second trigger signal at 2:00 a.m.; if the actual sleep information is acquired eight times by the sleep information acquisition module between 2:00 and 4:00 a.m., and the actual sleep information goes beyond the normal sleep information range five times, the processing module generates the third trigger signal at 4:00 a.m., and the audio play module 50 sends out the audio signal. The audio play module 50 may be a module jointly mounted with other modules of the snore stopping device or a separate external module, as long as the third trigger signal can control the audio play module 50.

The snore stopping device further includes a setting module (not shown), which is used for setting the preset stimulation time, the preset acquisition time period, the preset value, the first preset voltage and the second preset voltage. Thus, the user can set the preset stimulation time, the preset acquisition time period, the preset value, the first preset voltage and the second preset voltage according to actual conditions of himself/herself. It should be understood that, although each parameter value above can be set by the user himself/herself, each parameter value should fall into a corresponding set range, to avoid influencing sleep due to improper setting for the parameter values by the user.

The snore stopping device further includes a storage module 40, which is used for storing the actual sleep information acquired by the sleep information acquisition module 10, to facilitate the processing module 20 counting the number of occurrences of the actual sleep information going beyond the normal sleep information range within the preset acquisition time period from the time when the first trigger signal or the second trigger signal is generated. The audio signal sent out by the audio play module 50 may also be pre-stored in the storage module 40.

The snore stopping device further includes a mounting shell; the sleep information acquisition module 10, the processing module 20, the stimulation control unit 31 and the electric signal generating unit 32 are all mounted in the mounting shell; and the stimulation electrode 33 may be arranged outside the mounting shell. When the snore stopping device includes the storage module 40, the storage module 40 may also be arranged in the mounting shell.

Specifically, the mounting shell includes a wristband, a finger ring or a head band, to facilitate wearing without influencing sleep.

It could be understood that the above embodiments are merely exemplary embodiments adopted for describing the principle of the present invention, but the present invention is not limited thereto. Various variations and improvements may be made by those of ordinary skill in the art without departing from the spirit and essence of the present invention, and these variations and improvements shall also be encompassed within the protection scope of the present invention.

The invention claimed is:

1. A snore stopping device, comprising:
    a sleep information acquisition module, used for acquiring an actual sleep information of a user;
    a processing module, used for comparing the actual sleep information acquired by the sleep information acquisition module with a normal sleep information range, and generating a trigger signal when the actual sleep information goes beyond the normal sleep information range; and
    an electric stimulation module, used for contacting skin of the user and generating an electric stimulation signal according to the trigger signal;
    wherein the electric stimulation module comprises:
    a stimulation control unit, used for generating a control signal according to the trigger signal;
    an electric signal generating unit, used for generating an electric signal of preset voltage according to the control signal, and lasting the electric signal of the preset voltage for preset stimulation time; and
    a stimulation electrode, used for contacting the skin of the user and capable of generating the electric stimulation signal in a manner of discharging to the skin of the user after receiving the electric signal of the preset voltage;
    wherein the sleep information acquisition module is capable of periodically acquiring the actual sleep information of the user;
    the trigger signal comprises a first trigger signal and a second trigger signal, wherein when the sleep information acquisition module acquires the actual sleep information going beyond the normal sleep information range for the first time, the processing module generates the first trigger signal; after the processing module generates the first trigger signal, the processing module counts the number of occurrences of the actual sleep information going beyond the normal sleep information range within a preset acquisition time period from the time when the first trigger signal is generated, and generates the second trigger signal when the number of occurrences is greater than or equal to the preset value;
    the control signal comprises a first control signal corresponding to the first trigger signal and a second control signal corresponding to the second trigger signal; and
    the preset voltage comprises a first preset voltage corresponding to the first control signal and a second preset voltage corresponding to the second control signal, and the second preset voltage is greater than the first preset voltage.

2. The snore stopping device of claim 1, wherein the actual sleep information is a volume of snore produced by the user during sleep, and the sleep information acquisition module comprises a volume detecting device for detecting the volume of the snore.

3. The snore stopping device of claim 2, wherein a range of the normal sleep information is from 0 dB to 40 dB.

4. The snore stopping device of claim 1, wherein the stimulation electrode comprises a plurality of electrode plates and a pad for wrapping the electrode plates, the pad is provided therein with openings, the electrode plates are electrically connected with the electric signal generating unit, and at least part of each of the plurality of electrode plates is exposed by the opening to contact the skin of the user.

5. The snore stopping device of claim 4, wherein a conductive adhesive is arranged on the surface of the part of the electrode plate exposed by the opening.

6. The snore stopping device of claim 1, wherein the electric signal generating unit comprises a signal generator, which is electrically connected with the stimulation control unit and the stimulation electrode, respectively, and used for generating the electric signal of the preset voltage.

7. The snore stopping device of claim 1, wherein the electric signal generating unit comprises a signal generator, a first switch, a second switch and an amplifier;
    a control terminal of the first switch is connected with an output terminal of the stimulation control unit, an input terminal of the first switch is connected with an output terminal of the signal generator, an output terminal of the first switch is connected with the stimulation electrode, a control terminal of the second switch is connected with the output terminal of the stimulation control unit, an input terminal of the second switch is connected with the output terminal of the signal generator, an output terminal of the second switch is connected with an input terminal of the amplifier, an output terminal of the amplifier is connected with the stimulation electrode, and an input terminal of the signal generator is connected with the output terminal of the stimulation control unit; the first control signal is capable of controlling the first switch to be switched on and the second switch to be switched off, and the second control signal is capable of controlling the first switch to be switched off and the second switch to be switched on; and
    the signal generator is used for generating an electric signal of the first preset voltage, and the amplifier is capable of amplify the electric signal of the first preset voltage to an electric signal of the second preset voltage.

8. The snore stopping device of claim 1, wherein the trigger signal further comprises a third trigger signal, and the processing module counts the number of occurrences of the actual sleep information going beyond the normal sleep information range within a preset acquisition time period from the time when the second trigger signal is generated, and generates the third trigger signal when the number of occurrences is greater than or equal to the preset value; and
    the snore stopping device further comprises an audio play module, which is used for sending out an audio signal according to the third trigger signal.

9. The snore stopping device of claim 1, further comprising a setting module, which is used for setting the preset stimulation time, the preset acquisition time period, the preset value, the first preset voltage and the second preset voltage.

10. The snore stopping device of claim 1, further comprising a storage module, which is used for storing the actual sleep information acquired by the sleep information acquisition module.

11. The snore stopping device of claim 1, further comprising a mounting shell, wherein the sleep information acquisition module, the processing module, the electric signal generating unit and the stimulation control unit are all mounted in the mounting shell.

12. The snore stopping device of claim 11, wherein the mounting shell comprises a wristband, a finger ring or a head band.

* * * * *